US005728812A

United States Patent [19]

Koren et al.

[11] Patent Number: 5,728,812
[45] Date of Patent: Mar. 17, 1998

[54] ANTI-IDIOTYPIC ANTIBODY COMPOSITION FOR INHIBITING ACUTE COMPLEMENT-MEDIATED CYTOTOXICITY

[75] Inventors: Eugen Koren; David K. C. Cooper, both of Oklahoma City, Okla.

[73] Assignees: Oklahoma Medical Research Foundation; Baptist Medical Center of Oklahoma, Inc., both of Oklahoma City, Okla.

[21] Appl. No.: 458,274

[22] Filed: Jun. 2, 1995

Related U.S. Application Data

[62] Division of Ser. No. 133,934, Oct. 12, 1993, Pat. No. 5,560,911.
[51] Int. Cl.$^6$ .......................... C07K 16/42; C07K 16/18
[52] U.S. Cl. .......................... 530/387.2; 530/387.1; 530/387.5; 530/391.3; 530/391.1
[58] Field of Search .......................... 530/387.2, 387.1, 530/387.5, 391.1, 391.3

[56] References Cited

U.S. PATENT DOCUMENTS 5,215,904  6/1993  Gould et al. .......................... 435/172.3

FOREIGN PATENT DOCUMENTS 0325847  2/1989  European Pat. Off. .

OTHER PUBLICATIONS

Geller, R.L. et al, Transplantation, 55:168–172, Jan. 1, 1993.
Reed., E. et al NEJM, 316:1450–1455, 1987.
Galili, U. et al, J Exp Med, 160:1519–1531, Nov. 1984.
Fischel, R. J. et al., Transplantation Proceedings, 22(3):1077–1078, 1990.
Sandrin, M. S. et al., PNAS, 90:11391–11395, Dec. 1993.
Abdou, N.J., et al., "In Vitro Suppression of Serum Anti-DNA Antibody Binding to DNA by Anti-Idiotypic Antibody in Systemic Lupus Erythematosus", *J. Clin. Invest.*, 67:1297–1304 (May, 1981).
Bach, F.H., et al., "Accomodation: A Working Paradigm for Progressing Toward Clinical Discordant Xenografting", *Transplant. Proc.*, 23(1):205–207 (Feb., 1991).
Brodsky, F.M., et al., "Evolution of HLA Antigenic Determinants: Species Cross–reactions of Monoclonal Antibodies", *Immunogenetics*, 155:151–166 (1982).
Clackson, T., et al., "Making Antibody Fragments Using Phage Display Libraries", *Nature*, 352:624–688 I(Aug. 1991).
Cooper, D.K.C., et al., "The Pig as Potential Organ Donor for Man", *Xenotransplantation*, Springer–Verlag:481–500 (1991).
Cooper, D.K.C., et al., "Effects of Cyclosporine and Antibody Adsorption on Pig Cardiac Xenograft Survival in the Baboon", *J. Heart Transplant*, 7:238–246 (May/Jun., 1988).

Cooper, D.K.C., "Immediate Postoperative Care and Maintenance Immunosuppresive Therapy", 89–100 in Cooper, D.K.C. and Novitzky, D., eds., *The Transplantation and Replacement of Thoracic Organs*, (Kluwer, Dordrecht 1990).
Daugherty, B.L., et al., "Polymerase Chain Reaction Facilitates the Cloning, CDR–Grafting, and Rapid Expression of a Murine Monoclonal Antibody Directed Against the CD18 Component of Leukocyte Integrins", *Nucl. Acids Res.*, 19:2471–2476 (1991).
Galili, U., et al., "A Unique Natural Human IgG Antibody with Anti–α–Galactosyl Specificity", *J. Exp. Med.*, 160:1519–1531 (Nov., 1984).
Galili, U., et al., "Interaction Between Human Natural Anti–α–Galactosyl Immunoblobulin G and Bacteria of the Human Flora", *Infection and Immunity*, 56(7):1730–1737 (Jul., 1988).
Garver, J.J., et al., "Evidence of Similar Organization of the Chromosomes Carrying the Major Histocompatibility Complex in Man and Other Primates", *Cytogenetics & Cell Genetics*, 27:238–245 (1980).
Geller, R.L., et al., "Evidence that Polyreactaive Antibodies are Deposited in Rejected Discordant Xenografts", *Transplantation*, 55:168–172 (Jan., 1993).
Good, A.H., et al., "Identification of Carbohydrate Structures that Bind Human Antiporcine Antibodies: Implications for Discordant Xenografting in Humans", *Transplant Proc.*, 24(2):559–652 (Apr., 1992).
Hammer, C., "Evolutionary Considerations in Xenotransplantation", *Xenograft*, 25:115–123 (1989).
Hammer, C., et al., "Evolutionary, Physiological, and Immunological Considerations in Defining a Suitable Donor for Man", *Xenotransplantation*, 429–438 (1991).
Jerne, N.K., et al., "Recurrent Idiotopes and Internal images", *EMBO Journal*, 1:243–247 (Feb., 1982).

(List continued on next page.)

*Primary Examiner*—Susan A. Loring
*Attorney, Agent, or Firm*—Arnall Golden & Gregory, LLP

[57] ABSTRACT

Antibodies directed against idiotypes on naturally occurring human anti-animal antibodies are disclosed for use in inhibiting xenograft rejection in human patients. An effective quantity of these anti-idiotypic antibodies is injected into the actual or potential xenograft recipient in order to bind to the idiotypes expressed on anti-animal antibodies as well as subpopulations of B lymphocytes, to inhibit hyperacute rejection of transplanted animal tissues or organs by the human patient. Alternatively, anti-idiotypic antibodies are used in the form of immunoaffinity columns to deplete anti-animal antibodies from the recipient's serum. Methods of making mouse monoclonal, mouse recombinant, and human recombinant anti-idiotypic antibodies are described, as well as immunoaffinity columns containing immobilized anti-idiotypic antibodies. A method and means for assessing the expected character and severity of a patient's rejection response to transplanted animal tissues is described, as well as methods of identification, isolation and suppression of lymphocytes bearing anti-animal idiotypes.

14 Claims, No Drawings

OTHER PUBLICATIONS

Koren, E., et al., "Heterogeneity of Preformed Human Antipig Xenogeneic Antibodies", *Transplant Proc.*, 24(2):598–601 (Apr. 1992).

Lexer, G., et al., "Hyperacute Rejection in a Discordant (Pig to Baboon) Cardiac Xenograft Model", *J. Heart Transplant*, 4:411–418 (1986).

McCafferty, J., et al., "Phage Antibodies: Filamentous Phage Displaying Antibody Variable Domains", *Nature*, 348:552–554 (Dec., 1990).

Meeker, T.C.J., et al., "A Clinical Trial of Anti–Idiotype Therapy for B Cell Malignancy", *Blood*, 65:1349–1355 (Jun. 1985).

Michler, R.E., et al., "Prolongation of Primate Cardiac Xenograft Survival with Cyclosporine", *Transplantation*, 44(5):632–636 (Nov., 1987).

Miyajima, T., et al., "Anti–Idiotypic Antibodies in a Patient with a Functioning Renal Graft", *Nature*, 283:306–308 (Jan., 1980).

Neubauer, R.H., et al., "Reactaivity of Monoclonal Antibodies Against Human Leucocyte Antigens with Lymphocytes of Non–Human Primate Origin", *J. Immunogenetics*, 8:433–442 (Dec., 1981).

Norman, D.J., et al., "Consensus Statement Regarding OKT3–Induced Cytokine–Release Syndrome and Human Antimouse Antibodies", *Transplant Proc.*, 25(2):1:89–92 (Apr., 1993).

Oosterlaken, T.A.M., et al., "A Neutralization–Inhibition Enzyme Immunoassay for Anti–Idiotypic Antibodies that Block Monoclonal Antibodies Neutralizing Semliki Forest Virus", *J. Immunol. Methods*, 115:255—261 (1988).

Paul, L.C., et al., "Mechanism of Humoral Xenograft Rejection", *Xenotransplantation*, 47–67 (1991).

Platt, J.L., et al., "Mechanism of Tissue Injury in Hyperacute Xenograft Rejection", *Xenotransplantation*, 69–79 (Aug., 1991).

Platt, J.L., et al., "Immunopathology of Hyperacute Xenograft Rejection in a Swine–to–Primate Model", *Transplantation*, 52(2):214–220 (1991).

Polanka, E., et al., "Anti–Idiotypic Antibodies to HLA After Donor–Specific Blood Transfusion (DST)", *Transplant. Proc.*, 21:1806–1809 (Feb., 19890.

Reed, E., et al., "Effect of Antiidiotypic Antibodies to HLA on Graft Survival in Renal–Allograft Recipients", *New Engl. J. Med.*, 316:1450–1455 (Jun. 1987).

Reed, E., et al., "Effect of Anti–HLA and Anti–Idiotypic Antibodies on the Long–Term Survival of Heart and Kidney Allografts", *Transplant. Proc.*, 24:2494–2495.

Rodey, J.E., et al., "Association of Antiidiotypic Antibody with Successful Second Transplant of a Kidney Sharing HLA Antigens with the Previous Hyperacutely Rejected First Kidney", *Transplantation*, 48:54–57 (Jul., 1989).

Sasaki, T., et al., "Selective Elimination of Anti–DNA Antibody–producing Cells by Antiidiotypic Antibody Conjugated with Neocarzinostatin", *J. Clin. Invest.*, 77:1382–1386 (1986).

Simpson, M.A., et al., "Immunosuppression in Xenotransplantation", *Xenograft*, 25:273–284 (1989).

Somerville, C.A., et al., "Future Directions in Transplantation: Xenotransplantation", *Kidney Int.*, 44(42):S112–S121 (1993).

Stark, J.H., et al., "Immunological Compatibility Between the Chacma Baboon and Man", *Transplantation*, 52(6):1072–1078 (Dec., 1991).

Tsujisaki, M., et al., "A Sandwich Assay to Detect and Characterize Syngeneic Anti–Idiotypic Antibodies to murine Anti–HLA and Tumor Associated Associated Antigen Monoclonal Antibodies", *J. Immunol. Methods*, 95:47–55 (1986).

Welsh, K.I., et al., "Human Antibodies to Pig Determinants and Their Association with Hyperacute Rejection of Xenografts", *Xenotransplanation*, 501–510 (1991).

Werner, R.G., et al., "Safety and Economic Aspects of Continuous Mammalian Cell Culture", *Biotechnol.*, 22:51–68 (1992).

Ye, Y., Cooper, et al., "Experimental Xenotransplantation in Nonhuman Primates Using Distantly Related Donor Species", *Xenotransplantation*, 389–393 (1991).

Cooper, D.K.C., "Is Xenotransplantation a Realistic Clinical Option?," *Trans. Proc.* 24(5):2393–2396 (1992).

Salamé, et al., "Rejet hyperaigu xénogénique: tentative de traitement a l'aide d'anticorps anti–idiotypiques," *La Presse Médicale* 21, n° 41:1945–1946 (1992).

ANTI-IDIOTYPIC ANTIBODY COMPOSITION FOR INHIBITING ACUTE COMPLEMENT-MEDIATED CYTOTOXICITY

This is a divisional of application U.S. Ser. No. 08/133,934 filed on Oct. 12, 1993, by Eugen Koren and David K. C. Cooper entitled "Anti-Idiotypic Antibody Composition for Inhibiting Acute Complement-Medicated Cytotoxicity" issued as U.S. Pat. No. 5,560,911.

The present invention is in the field of organ transplantation, and more particularly in the area of prevention of xenograft rejection.

BACKGROUND OF THE INVENTION

The demand for human organs and tissues suitable for transplantation is steadily increasing. The gap between the demand and the availability of organs is very likely to grow even wider in view of the continuing improvements in transplantation procedures and outcome. A potential answer to this problem is the use of non-human primate organs. However, these animals are in short supply worldwide, and are considered to be endangered species.

The pig is a potential donor because of compatible physiological characteristics (Cooper, D. K. C., et al., *Xenotransplantation*, Springer-Verlag:481–500, 1991; Tumbleson, M. E. (ed.), *Swine in Biomedical Research*, Volume 3 (Plenum Press, New York, 1985); Stanton, H. C., et al. (eds.), *Swine in Cardiovascular Research*, Volumes I–III (CRC Press, Inc., Boca Raton, 1986)), size, breeding properties and maintenance costs. Organ transplantation between widely disparate species such as pig and man, however, is followed by antibody-mediated hyperacute rejection within minutes. If the problem of antibody-mediated rejection could be overcome, then pig to human xenotransplantation might be possible. If the hyperacute rejection is prevented, a pig organ transplanted into a human recipient may survive for a longer period than would be otherwise possible due to the "accommodation" (Bach, F. H., et al., *Transplant. Proc.*, 23:205, 1991) of the organ and to the therapeutic suppression of cellular rejection (Simpson, M. A., et al., in Hardy, M. A. (ed.), *Xenograft 25*, 273–284 (Elsevier N.Y. 1989); Michler, R. E., et al., *Transplantation*, 44(5): 632–636, 1987).

Antibody-mediated Rejection of Pig Tissue

Human natural or preformed antibodies play a significant role in hyperacute rejection of pig organs (Welsh, K. I., et al., in Cooper, D. K. C., et al. (eds.), *Xenotransplantation*, 501–510 (Springer-Verlag 1991); Paul, L. C., in Cooper, D. K. C., et al. (eds.), *Xenotransplantation*, 47–67 (Springer-Verlag 1991); Platt, J. L., et al., in Cooper, D. K. C., et al. (eds.), *Xenotransplantation*, 69–79 (Springer-Verlag 1991); Somerville, C. A., et al., *Kidney Int.*, 44, Suppl. 42:S112–S121, 1993). Recent experiments strongly indicate that human natural antibodies directed against the αGal (1→3)βGal carbohydrate structure, referred to herein as "anti-gal antibodies", are the major factor in the hyperacute rejection of pig cells and organs (Good, A. H., Cooper, D. K. C., et al., *Transplant Proc.*, 24(2):559–652, 1992). These antibodies bind to pig cells, which, like cells of most subprimate mammals, express αGal(1→3)Gal on their surfaces. Anti-gal antibodies bind to the cell surface, activate the complement system, and thus cause cell damage.

In one approach, described in U.S. Ser. No. 08/049,817, filed Apr. 20, 1993, by D. K. C. Cooper and E. Koren, entitled, "Genetically Engineered Animals for Use as Organ Donors," a genetically-engineered animal, such as a pig, which is deficient in the α 1→3 galactosyl transferase gene, resulting in non-expression of galactosyl epitopes on its organs and tissues is constructed. However, this method does not address the problem of hyperacute rejection at its source: the immunologic response by the recipient to the transplanted tissue.

In a second approach, hyperacute rejection can be inhibited by the addition of oligosaccharides with terminal αGal (1→3)βGal residues to human plasma, which competitively inhibit binding of these naturally occurring antibodies to the xenograft. Alternatively, the same αGal(1→3)βGal containing oligosaccharides immobilized to a solid support can be used as immunoaffinity adsorbers to remove anti-gal antibodies from the blood. These two approaches can be applied in complementary fashion with even better prospects for successful prevention of hyperacute rejection of pig organs. U.S. Ser. No. 07/933,466, filed Aug. 21, 1992, by Good, et al., now U.S. Pat. No. 5,651,968 discloses the use of both immunoaffinity adsorbers and parenteral administration of αGal(1→3)βGal containing oligosaccharides to inhibit hyperacute rejection of pig organs.

However, anti-gal antibodies bind to α-gal oligosaccharides with relatively low affinity. This could necessitate a high concentration of oligosaccharides in the transplant recipient's blood in order to block the binding of circulating antibodies to the transplanted organ. This could result in side effects due to the high concentrations of carbohydrate. Moreover, the carbohydrate is relatively expensive to make, and treatment would be expensive. The low binding affinity could also have an adverse impact on extracorporeal immunoaffinity treatment by making the removal of anti-gal antibodies relatively inefficient.

Furthermore, anti-gal antibodies, although important in xenograft rejection, may not be the only human anti-pig antibodies responsible for hyperacute rejection. Anti-pig antibodies that bind to the protein components on the surface of pig cells have also been reported (Tuso, P. J., et al., Presentation at the American Society of Transplant Surgeons, 12th Annual Meeting in Houston, May 17–19, 1993). In addition, individual differences in profiles of anti-pig antibodies may exist among potential recipients. Some patients are likely to have less anti-gal antibodies, and more of the "non anti-gal" antibodies.

It is therefore an object of the present invention to provide a method for inhibiting antibody-mediated rejection of xenografts in human patients.

It is a further object of the present invention to provide a means for depleting anti-xenotransplant antibodies from human blood.

It is another object of the present invention to provide a means for quantification and suppression in transplant recipients of lymphocytes involved in production of anti-xenotransplant antibodies.

It is another object of the invention to provide a means for predicting the severity of xenotransplant rejection in human recipients.

SUMMARY OF THE INVENTION

Antibodies directed against idiotypes on naturally occurring human anti-animal antibodies are disclosed for use in inhibiting xenograft rejection in human patients. An effective quantity of these anti-idiotypic antibodies is injected into the xenograft recipient in order to bind to the idiotypes expressed on anti-xenograft antibodies, especially anti-pig antibodies, as well as subpopulations of B lymphocytes, to inhibit rejection of transplanted xenografts, especially pig tissues, by the human patient.

Methods of making mouse monoclonal and human anti-idiotypic antibodies are described, as well as immunoaffinity columns containing immobilized anti-idiotypic antibodies, and a method and means for assessing the expected character and severity of a patient's rejection response to transplanted xenografts. Also described are methods of identification, isolation and suppression of lymphocytes bearing anti-animal idiotypes.

DETAILED DESCRIPTION OF THE INVENTION

Antibodies directed against idiotypes on naturally occurring human anti-xenograft antibodies are disclosed for use in inhibiting xenograft rejection in human patients. An effective quantity of these anti-idiotypic antibodies is injected into the xenograft recipient in order to bind to the idiotypes expressed on anti-xenograft antibodies as well as subpopulations of B lymphocytes, to inhibit hyperacute rejection of transplanted xenograft by the human patient.

As used herein, "hyperacute rejection" refers to rapid graft rejection, beginning minutes after implantation, and which is mediated by pre-existing antibodies to the graft.

As defined herein, a "xenograft" may be an organ, tissue, aggregates of cells, or cells, collectively referred to herein as "tissue". The tissue may be selected from any appropriate tissue of the body of the tissue donor. These tissues include, but are not limited to, heart, kidney, lung, islet cells, liver, bowel and skin cells.

Methods of making mouse monoclonal and human anti-idiotypic antibodies are described, as well as immunoaffinity columns containing immobilized anti-idiotypic antibodies, and a method and means for assessing the expected character and severity of a patient's rejection response to transplanted animal tissues. Also described are methods of identification, isolation and suppression of lymphocytes bearing anti-animal idiotypes.

As demonstrated by the examples, anti-idiotypic antibodies directed against idiotypes on human anti-pig antibodies bind to human anti-pig antibodies, and inhibit the hyperacute rejection of pig organs transplanted into human patients. As used herein, "anti-idiotypic antibodies" refers to antibodies binding to human anti-animal antibodies. Although in the preferred embodiment the anti-idiotypic antibodies are directed against anti-gal antibodies, anti-idiotypes can be prepared that bind to non-anti-gal anti-animal antibodies. Both types of anti-idiotypic antibodies are likely to be useful in neutralization of anti-animal antibodies that bind to glycoprotein, glycolipid and protein components present on the surface of animal cells. Since human and primate antibodies, especially baboon antibodies, are very similar, some of the anti-idiotypic antibodies against human anti-pig antibodies bind to baboon anti-pig antibodies.

Although described herein with specific reference to pigs, the same methodology can be used to generate anti-idiotype antibodies to xenografts from any species, including primates, for transplantation into man.

There are four mechanisms for obtaining anti-idiotypic antibodies that bind to human anti-xenotransplant antibodies:

1. Production of animal, for example, mouse, monoclonal anti-idiotypic antibodies which are optionally humanized prior to injection into humans;

2. Isolation of naturally occurring human anti-idiotypic antibodies;

3. Immunization of potential recipients of xenotransplants with anti-xenotransplant antibodies, or fragments thereof, in order to elicit production of anti-idiotypic antibodies; and 4. Isolation of human B lymphocytes which express anti-idiotypic antibodies, followed by production of recombinant human anti-idiotypic antibodies.

These methods are generally described below, and described in more detail in the following non-limiting examples.

Anti-idiotypic Antibodies

Anti-idiotypic antibodies recognize specific idiotypes that are antigenic determinants expressed within the variable regions of immunoglobulins, and have high specificity and affinity. Beneficial effects from the presence of naturally-occurring anti-idiotypic antibodies have been demonstrated by studies carried out in kidney allograft recipients over the last decade. The survival time of these allografts was significantly longer in some of the patients who received donor-specific blood transfusions (DST). When stimulated with the transfused blood cells, the immune system responds with antibodies directed against incompatible HLA molecules. At first this makes the recipient even more sensitized. However, the presence of anti-HLA antibodies subsequently elicits the production of anti-idiotypic antibodies capable of binding to idiotypes on anti-HLA antibodies and neutralizing their activity in the humoral rejection of the allograft (Miyajima, T., et al., Nature, 283:306–308, 1980; Reed, E., et al., New Engl. J. Med., 316:1450–1455, 1987; Polanka, E., et al., Transplant Proc., 21:1806–1809, 1989; Rodey, J. E., et al., Transplantation, 48:54–57, 1989; Reed, E., et al., Transplant Proc., 24:2494–2495, 1992).

Furthermore, subpopulations of B lymphocytes share the same idiotypes with antibodies. These lymphocytes, along with the corresponding antibodies, have the same specificity and represent an idiotypic network designed to counteract the corresponding antigens (Jerne, N. K., et al., EMBO Journal, 1:243–247, 1982). Therefore, an anti-idiotypic antibody occurring in a DST-treated kidney allograft recipient can neutralize the targeted anti-HLA antibody as well as B lymphocytes bearing the same idiotype. This mechanism is responsible for specific and long-lasting immunosuppression, allowing a prolonged survival of the graft.

Anti-idiotypes against anti-xenograft antibodies elicited in humans should at least in part inhibit rejection of the xenograft by human xenograft recipients. This effect is not limited to the patient's own anti-idiotypic antibodies. Monoclonal anti-idiotypic antibodies produced against specific human antibodies also bind to the corresponding idiotypes on antibody molecules and B lymphocytes (Meeker, T. C. J., et al., Blood, 65:1349–1355, 1985; Sasaki, T., et al., J. Clin. Invest., 77:1382–1386, 1986). A panel of carefully selected monoclonal anti-idiotypic antibodies directed against human anti-xenograft antibodies could also have a significant inhibitory effect on hyperacute rejection of pig xenografts.

Production of Anti-idiotypic Antibodies

1. Isolation of Human Anti-animal Antibodies

Anti-animal antibodies are isolated by perfusing pooled human serum through animal hearts, kidneys, or other organs until anti-animal antibodies are bound to the organs, followed by washing off the unbound serum components and the elution of adsorbed anti-animal antibodies.

The human anti-animal antibodies are used to immunize mice to generate anti-idiotypic antibodies.

2. Generation of Anti-idiotypic Antibodies

Appropriate animals, such as mice, are immunized with the isolated human anti-animal antibodies. In a preferred method, each mouse is injected biweekly with 50 µg of antibody with no adjuvant over a period of six months. Antibody production in the mice is then assayed using standard techniques for determining the titer of anti-idiotypic antibodies, for example, by measuring the ability of mouse sera to inhibit the binding of human anti-pig antibodies to fixed pig cells in a competitive enzyme-linked immunoassay (ELISA). The mice with the highest anti-idiotypic titer are then selected for production of hybridomas. Hybridomas are generated using standard techniques to fuse spleen cells from high-titer mice with mouse myeloma cells.

3. Creation of a Library of Anti-idiotypic Antibodies

The hybridomas are screened for those producing anti-idiotypic antibodies using the above competitive ELISA. In addition to the competitive ELISA, the binding of hybridoma antibodies to human and primate anti-animal antibodies is determined by a direct ELISA using plates coated with anti-animal antibodies. The hybridoma antibodies reactive with anti-animal antibodies are further tested for protective activity. The "Live/Dead" viability-cytotoxicity assay (Molecular Probes, Eugene, Oreg.) is carried out on cultured animal cells incubated with human or primate sera in the presence of hybridoma antibodies. Staining with the Live/Dead kit allows for clear distinction between live cells, which show cytoplasmic green fluorescence, and dead cells, which show dark cytoplasm and red fluorescent nuclei. The anti-idiotypic antibodies capable of protecting animal cells from the cytotoxic activity of human or baboon sera are identified. Protective anti-idiotypic antibodies are further assayed separately, and in various combinations. The highest level of protection is determined for each individual antibody and for all possible combinations thereof. A library of anti-idiotypic antibodies is established on the basis of these data.

4. Screening Potential Transplant Recipients for the Expected Severity of Rejection Response The library of protective anti-idiotypic antibodies is then analyzed against the serum samples of randomly selected human subjects in order to determine whether or not different patients require different hybridoma antibodies or different combinations and quantities of antibodies for inhibition of hyperacute rejection of animal cells.

Production of Recombinant Anti-idiotypic Antibodies

Hybridoma cells secreting selected protective anti-idiotypic antibodies are used in the production of recombinant anti-idiotypic antibodies. For example, Pharmacia's (Pharmacia LKB Biotechnology, Sweden) "Recombinant Phage Antibody System" (RPAS) may be used for this purpose. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody.

Using the antigen-driven screening system, the ScFv with binding characteristics equivalent to those of the original monoclonal antibody is selected (See, e.g., McCafferty, J., et al., Nature, 348:552–554, 1990; Clackson, T., et al., Nature, 352:624–688, 1991, incorporated herein by reference). The recombinant ScFv includes a considerably smaller number of epitopes than the intact monoclonal antibody, and thereby represents a much weaker immunogenic stimulus when injected into humans. An intravenous injection of ScFv into humans is, therefore, expected to be more efficient and immunologically tolerable in comparison with currently used whole monoclonal antibodies (Norman, D. J., et al., Transplant Proc., 25, suppl. 1:89–93, 1993).

Production of Humanized Recombinant Animal Anti-idiotypic Antibodies

If necessary, animal anti-idiotypic antibodies, such as murine anti-idiotypic antibodies, can be humanized to further reduce the transplant recipient's immune response to the animal antibodies. A humanized antibody is one in which only the antigen-recognition sites or complementarity-determining hypervariable regions (CDRs) are of non-human origin, and all framework regions (FR) of variable domains are products of human genes. In one method of humanization of an animal monoclonal anti-idiotypic antibody, RPAS is combined with the CDR grafting method described by Daugherty et al., Nucl. Acids Res., 19:2471–2476, 1991, incorporated herein by reference. Briefly, the variable region DNA of a selected animal recombinant anti-idiotypic ScFv is sequenced by the method of Clackson, T., et al., Nature, 352:624–688, 1991, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The expression of recombinant CDR-grafted immunoglobulin gene is accomplished by its transfection into human 293 cells (transformed primary embryonic kidney cells, commercially available from American Type Culture Collection, Rockville, Md. 20852) which secrete fully grafted antibody. See, e.g., Daugherty, B. L., et al., Nucl. Acids Res., 19:2471–2476, 1991, incorporated herein by reference. Alternatively, humanized ScFv is expressed on the surface of bacteriophage and produced in E. coli as in the RPAS method described above.

Intravenous Administration of Anti-idiotypic Antibodies to Prevent Xenograft Rejection The recombinant ScFv or humanized anti-idiotypic antibodies directed against anti-animal antibodies described herein may be administered intravenously to a transplant recipient in order to inhibit the hyperacute rejection of transplanted animal tissues. These antibodies are produced in bioreactors in large quantities and processed for the parenteral use in humans according to established procedures, for example, as described by Werner, et al., J. Biotechnology, 22:51–63, 1992, the teachings of which are incorporated herein by reference. The anti-idiotypic antibodies are administered in an appropriate pharmaceutical carrier, such as saline. The preferred routes of administration are by intravenous infusion and intravenous injection, although intramuscular injection is possible.

Based on the concentration of anti-gal antibodies present in human serum (Galili, U., et al., J. Exp. Med., 160:1519–1531, 1984), and an estimated probable contribution of non-anti-gal anti-pig antibodies, it is estimated that an adult human recipient would be treated with a total of 5–8 grams of anti-idiotypic antibodies, in an appropriate pharmaceutical carrier, over a period of three weeks. Two grams would be administered by i.v. infusion several hours prior to and lasting throughout the transplant surgery. This would be followed with i.v. injections of 0.5 grams of antibody every three days. It is expected that accommodation would take place within the three-week period following surgery, and that the danger of hyperacute antibody-mediated rejection would be minimized. The recipient would also be maintained on a standard pharmacologic immunosuppressive regime, for example, consisting of cyclosporine to maintain a whole blood level of 200–300 ng/ml, as measured by HPLC, cyclophosphamide at the dosage of 0.5–2 mg/kg/day, and prednisone at 1 mg/kg/day in divided doses (Cooper, D. K. C., *Immediate Postoperative Care and Maintenance Immunosuppressive Therapy*, pp. 89–100 in Cooper, D. K. C. and Novitzky, D., eds., *The Transplantation and Replacement of Thoracic Organs* (Kluwer, Dordrecht 1990)).

Minimization of Possible Side-effects

Possible side effects of anti-idiotypic antibody administration include the generation of human anti-murine antibodies in the recipient, despite the fact that recombinant and humanized anti-idiotypic antibodies are not as immunogenic as whole animal immunoglobulin. If human anti-animal antibodies do arise in the recipient, they could diminish the protective activity of anti-idiotypic antibodies. These side effects could be reduced by administration of lower intravenous dosage of anti-idiotypic antibodies in conjunction with extracorporeal removal of anti-animal antibodies, as described below.

Alternatively, the anti-idiotypic antibodies could be used in combination with administration of oligosaccharides present in the animal cells which are recognized by the human patient as foreign. A preferred method would be removal of circulating anti-pig antibodies with the anti-idiotypic antibodies immobilized on a column, followed by parenteral administration of oligosaccharides, in the case of pig xenotransplantation, α-gal oligosaccharides. The high-affinity monoclonal immunosorber would ensure significant removal of anti-gal and other anti-animal antibodies from the circulation. The remaining traces of anti-animal antibodies, as well as newly synthesized anti-gal antibodies, would then be neutralized with oligosaccharides. Oligosaccharides are known to be virtually non-antigenic in the absence of protein.

The immune response against anti-idiotypic antibodies may also be minimized by the use of human recombinant antibodies, described below.

Advantages of Anti-idiotypic Antibodies

In the preferred embodiment, properly selected anti-idiotypic antibodies directed against idiotypes on human anti-animal antibodies can overcome the problems potentially arising from the low binding affinity between oligosaccharides and anti-gal antibodies, as well as remove non-anti-gal antibodies, in addition to the anti-gal antibodies, which may be instrumental in xenograft rejection. First, association constants between anti-idiotypic antibodies and their targets, i.e., idiotypes on immunoglobulin molecules, vary between $10^8$ and $10^{11}$M. Association constants between carbohydrate epitopes and antibodies usually range between $10^5$ to $10^6$M. Therefore, anti-idiotype/idiotype interactions are characterized by affinities that are several orders of magnitude higher than carbohydrate-antibody interactions. Furthermore, affinity and avidity of monoclonal anti-idiotypic antibodies can be increased even further using the above-described recombinant antibody methodology.

Primate Model for Testing and Application of Useful Antibodies and Dosages Thereof Due to the many similarities between human and baboon immune systems (Neubauer, R. H., et al., *J. Immunogenetics*, 8:433–442, 1981; Garret, J. J., et al., *Cytogenetics & Cell Genetics*, 27:238–245, 1980; Brodsky, F. M., et al., *Immunogenetics*, 155:151–166, 1982; Hammer, C., in Hardy, M. A. (ed.), *Xenograft* 25, 115–123 (Elsevier N.Y., 1989); Stark, J. H., et al., *Transplantation*, 52(6):1072–1078 (Dec. 1991); Hammer, C., in Cooper, D. K. C., et al. (eds.), *Xenotransplantation*, 429–438 (Springer-Verlag 1991)), and because of the large size of baboons, these animals are convenient experimental model recipients of pig organs. These non-human primates also express anti-pig antibodies, and reject pig organs hyperacutely (Lexer, G., et al., *J. Heart Transplant*, 4:411–418, 1986; Ye, Y., Cooper, D. K. C., in Cooper, D. K. C., et al. (eds.), *Xenotransplantation*, 389–393 (Springer-Verlag 1991); Cooper, D. K. C., et al., *J. Heart Transplant*, 7:238–246, 1988; Platt, J. L., et al., *Transplantation*, 52(2):214–220, 1991). As human and baboon immunoglobulins are structurally very similar, some of the anti-idiotypic antibodies against human anti-pig antibodies should bind to baboon anti-pig antibodies and inhibit rejection of pig to baboon xenografts. For instance, Geller, R. L., et al., *Transplantation*, 55:168–172, 1993, have described an idiotype shared between human and baboon anti-pig antibodies.

Immobilization of Anti-idiotypic Antibodies and Preparation of Immunoaffinity Columns For diagnostic purposes, as well as for treatment of xenograft recipients, anti-idiotypic antibodies are covalently coupled to an insoluble matrix. Suitable anti-idiotypic antibodies are selected based on their protective activity, affinity, chemical stability and immunoglobulin class. Preferred antibodies are stable IgG anti-idiotypic antibodies with high protective activity against anti-pig antibodies, as well as high binding affinity. These anti-idiotypic antibodies are purified using procedures well-known to those skilled in the art.

Purified anti-idiotypic antibody may be immobilized using coupling kits consisting of various forms of activated gels, for example, Affi-Gel™ or Affi-Prep™ (Bio-Rad, Richmond, Calif.), ImmunoPure™ Ag/AB Immobilization kits 1,2 and 3 (Pierce, Rockford, Ill.), and appropriate reagents, although other methods of antibody immobilization are well-known to those skilled in the art. Immunoaffinity columns containing immobilized anti-idiotypic antibodies can be used for the removal and isolation of anti-animal antibodies from patient blood. Extracorporeal reactors, such as dialysis or plasmapheresis machines, are readily adapted for this procedure by methods well-known to those skilled in the art.

Immobilized monoclonal anti-idiotypic antibodies are also used for the isolation and separation of anti-animal antibodies of the highest purity. All of the separated anti-animal antibodies are analyzed and categorized according to their cytotoxic effects on animal cells. A categorization of anti-idiotypic antibodies is also made according to the correspondence of each antibody with its anti-animal antibody counterpart. The higher the cytotoxic activity of the anti-animal antibody, the more important is its corresponding anti-idiotypic antibody in inhibiting hyperacute rejection of transplanted animal tissue.

Recipient's Profile of Anti-animal Antibodies

Anti-gal antibodies represent an important fraction of human anti-pig antibodies. The human body produces anti-gal antibodies in response to common bacterial antigens present in gastrointestinal and respiratory systems (Galili, U., et al., *Infection and Immunity*, 56(7):1730–1737, 1988). The variability of intestinal and respiratory bacterial flora, as well as the diversity of immune response among individuals, very strongly suggests the existence of subpopulations and variable profiles of anti-gal antibodies in potential recipients.

The same is expected to be true of non anti-gal antibodies. Although the diversity of anti-animal antibodies is probably considerable, a comprehensive library of anti-idiotypic antibodies should correspond to all important subpopulations of anti-animal antibodies.

The two sets of antibodies, purified anti-animal antibodies and the corresponding anti-idiotypic antibodies, can be used in a competitive binding immunoassay to determine the profile of anti-animal antibodies in each potential recipient prior to transplantation. The biotinylated, purified and characterized anti-pig antibody is mixed with a sample of the recipient's serum and allowed to bind to the corresponding anti-idiotypic antibody adsorbed on a micro-ELISA plate. The binding of biotinylated antibody is quantified by observation of the colored reaction which occurs after addition of streptavidin-peroxidase and peroxidase substrate. As the anti-animal antibody present in the recipient's serum competes for the anti-idiotypic antibody on the plate it inhibits the binding of the biotinylated antibody. This lowers the intensity of the colored reaction proportionally to the concentration of the anti-animal antibody. A battery of immunoassays including all anti-animal antibodies with significant cytotoxic activity can be used to determine anti-animal antibody profiles in potential recipients.

Anti-animal antibody profiles characterized by highly cytotoxic antibodies are likely to be associated with the most severe xenograft transplant rejection. In such cases, the preoperative immunoabsorption of anti-animal antibodies should be intensified. Knowledge of the recipient's anti-animal antibody profile is also helpful in selecting the most suitable immunosorbers designed to specifically remove anti-animal antibodies actually present in the recipient's blood.

Immunization of Potential Recipients with Anti-animal Antibodies

Anti-idiotypic antibodies directed against anti-animal antibodies occurring in humans could inhibit rejection of animal to human xenografts. Such anti-idiotypic antibodies could be elicited by immunization with the purified anti-animal antibodies isolated with mouse monoclonal anti-idiotypic antibody columns described herein. Although the intact immunoglobulin molecules could be used, the $Fab_1$ or $Fab_2$ fragments would have a greater chance to elicit production of anti-idiotypic antibodies in the recipient. A library of appropriate anti-animal $Fab_1$ or $Fab_2$ fragments would be established, and recipients would be immunized only with those anti-animal antibodies that are detected in their respective sera.

The potential recipients of animal organs would be immunized prior to the transplantation. In one embodiment, the potential recipients would be immunized prior to the transplantation over a period of 6-8 weeks by 3-4 intramuscular or subcutaneous injections of 400-800 micrograms, preferably 400-600 micrograms, of anti-animal $Fab_1$ or $Fab_2$. The recipients would also be monitored for the anti-idiotypic response and concomitant decrease in cytotoxicity of recipient's serum towards cultured animal cells. The transplantation would be carried out at the optimal time, based on the cytotoxic activity of the recipient's serum against cultured animal cells. A decrease in serum cytotoxicity of 50% or higher would be considered satisfactory before the transplantation. The immunization approach would be applied in patients who are not in immediate need of xenografts, but are considered candidates for xenotransplant within several months.

Quantification and Suppression of B Lymphocytes Bearing Anti-animal Idiotypes

The same idiotypes are shared between a circulating antibody and the B lymphocytes producing the antibody. For example, Geller, R. L., et al., *Transplantation*, 55:168–172, 1993, have shown that an idiotype is shared between the IgM anti-pig antibodies in human serum and the surface of some lymphocytes in the human spleen. Therefore, the mouse monoclonal anti-idiotypic antibodies should recognize both circulating anti-animal antibodies and their corresponding B-lymphocytes. Immunofluorescence staining of human peripheral blood mononuclear cells with mouse monoclonal anti-idiotypic antibodies provides two such examples. One of the antibodies ($E_2A_2$) described herein strongly stained the surface of some cells, whereas the other ($E_2C_3$) showed moderate staining. Both of these antibodies were able to protect 50–60% of cultured pig cells, as described below, indicating their specificity for the cytotoxic anti-pig antibodies. The cells stained with these anti-idiotypic antibodies may represent B-lymphocytes bearing corresponding idiotypes on their surface. The library of mouse monoclonal anti-idiotypic antibodies described herein is therefore likely to contain anti-idiotypic antibodies capable of recognizing idiotypes on the surface of B lymphocytes.

One method of quantification of B cells includes isolation of mononuclear cells from patients' peripheral blood by the histopaque method (Sigma, St. Louis, Mo.). The cells are incubated with mouse monoclonal anti-idiotypic antibody coupled with fluorescein isothiocyanate (FITC labeling kit, Pierce, Rockford, Ill.) in order to visualize cells with the surface-expressed idiotype. In addition to FITC-labeled anti-idiotypic antibody (green fluorescence), the cells are also stained with PerCP-labeled (red fluorescence) B-lymphocyte-specific monoclonal antibody Anti-Leu-12 (Becton Dickinson, San Jose, Calif.). This double staining procedure is followed by fluorescence analysis with Becton/Dickinson's FACScan using the two-color program. The subsets of B-lymphocytes bearing specific anti-pig idiotypes can then be accurately counted.

The number of lymphocytes bearing anti-pig idiotypes in a potential recipient could be used as predictor of the severity of rejection. A high number of anti-pig lymphocytes might be associated with more severe rejection of a xenograft, as well as faster regeneration of eliminated anti-pig antibodies.

Anti-idiotypic antibodies capable of binding to the surface of B lymphocytes could be also produced in the form of cytotoxic recombinant ScFvs using procedures well-known to those skilled in the art. See, e.g., George, A. J. T., *The Second Annual IBC International Conference on Antibody Engineering*, San Diego, Calif., Dec. 16–18, 1991, incorporated herein by reference. Intravenous administration of cytotoxic ScFv should deplete the recipient's B lymphocytes which produce the corresponding anti-animal antibody. This treatment could be administered both prior to and after the xenotransplantation in order to reduce both the production and regeneration of anti-animal antibodies. The dosage and frequency of administration would be based on the number of idiotype-bearing B lymphocytes present in peripheral blood. The objective would be to greatly reduce the number of these cells.

Detection of Naturally-occurring Human Anti-idiotypic Antibodies

Studies demonstrate that approximately 20% of the sera from individuals with blood group AB are less toxic to pig cells in vitro. Since neither the immunoglobulin nor complement concentrations were abnormal in these cases, naturally-occurring anti-idiotypic antibodies against anti-pig antibodies might be responsible for the lower cytotoxicity. Furthermore, the AB sera with lower cytoxic activity are capable of inhibiting the cytotoxicity of sera with higher cytotoxicity when the sera are mixed together. This inhibition is consistent with the presence of neutralizing anti-idiotypic antibodies in the sera with lower cytotoxic activity (Abdou, N. I., et al., *J. Clin. Invest.*, 67:1297–1304, 1981).

An enzyme linked immunosorbent assay (ELISA) is used as follows to detect and quantify naturally occurring human anti-idiotypic antibodies. ELISA plates are coated with purified anti-animal antibodies and blocked. The plates are then incubated with corresponding anti-idiotypic antibodies, preferably of murine origin, which are biotinylated at the Fc fragment using procedures well-known to those skilled in the art, e.g., using the biotinylation kit available from Pierce, Rockford, Ill. In order to determine the presence and concentration of naturally-occurring human anti-idiotypic antibody, the patient's serum is mixed with biotinylated anti-idiotypic antibody and added to the coated plate. Naturally-occurring human anti-idiotype is, therefore, competing with biotinylated anti-idiotype for anti-animal idiotype on the plate. The higher the concentration of human anti-idiotype in the serum, the lower will be the binding of biotinylated anti-idiotype to the plate. The magnitude of inhibition is determined by observation of the colored reaction occurring after an incubation with streptavidin-peroxidase and peroxidase substrate (Kirkegaard and Perry Labs, Gaithesburg, Md.).

Similar competitive immunoassays have been used for detection of anti-idiotypic antibodies (Tsujisaki, M., et al., *J. Immunol. Methods*, 95:47–55, 1986; Oosterlaken, T. A. M., et al., *J. Immunol. Methods*, 115:255–261, 1988). However, the present approach differs in that it uses characterized anti-animal antibodies as well as their corresponding monoclonal anti-idiotypic antibodies in order to precisely identify and quantify naturally-occurring human anti-idiotypic antibodies directed against human anti-animal antibodies. This method will also be useful in predicting the severity of hyperacute rejection and in monitoring anti-idiotypic antibodies in patients immunized with anti-animal antibodies, Fab$_1$, or Fab$_2$ fragments.

Production of Human Recombinant Anti-idiotypic Antibodies

Patients with relatively high titers of naturally-occurring anti-idiotypic antibodies, or patients with anti-idiotypic antibodies elicited by immunization, can be used as a source of B lymphocytes expressing anti-idiotypic antibodies. Peripheral blood mononuclear cells are first isolated by the above-described histopaque method. These cells are then fluorescently stained with selected FITC-labeled human anti-animal antibodies, and with PerCP-labeled anti-Leu12 antibody. The B lymphocytes expressing anti-idiotypic antibodies bind anti-animal antibodies to their surface and stain with green (FITC) as well as red (PerCP) fluorescence. Doubly-stained cells are isolated by the use of a laser-activated cell sorter (FACStar PLUS$_1$ Becton/Dickinson). These cells serve as a source of RNA enriched in mRNA encoding anti-idiotypic antibodies. The mRNA is then used in a polymerase chain reaction (PCR) to amplify heavy and light chain variable region genes.

In a similar fashion to the method described for preparation of the recombinant antibodies, the human ScFv are made and selected on the basis of their affinity for anti-animal antibodies (See, e.g., Huang, S. C., Koren, E., et al., *Human Recombinant Monoclonal Antibodies to 60kD Ro. Autoantigen,* American College of Rheumatology, 57th Annual Scientific Meeting, San Antonio, Nov. 7–11, 1993). Briefly, as described above, RNA enriched in mRNA encoding anti-idiotypic antibodies is obtained and amplified using the PCR. Genes encoding single chain Fv fragments are made by randomly combining the VH and VL products through a linker using PCR. This combinatorial library is then cloned into a phage system, and displayed on the surface of the phage using the method of Cambridge Antibody Technology. Anti-idiotypic ScFv-bearing phage are enriched by several rounds of growth and screening with anti-animal antibodies. Individual anti-idiotypic ScFv are then selected based on binding to anti-animal antibody as determined by ELISA.

Human recombinant anti-idiotypic ScFv directed against anti-animal antibodies would be used intravenously for inhibition of hyperacute rejection. The advantage of these reagents would be their minimal, or non-existent, immunogenicity to human recipients.

The anti-idiotypic antibodies described above and their use for inhibiting rejection of implanted pig tissue will be further understood by reference to the following non-limiting examples.

Example 1: Production of Mouse Monoclonal Anti-idiotypic Antibodies (a) Isolation of Human Natural Anti-pig Antibodies Two hundred ml of pooled human AB plasma were perfused through a pig heart three times at a flow rate of 10 ml/min. After perfusion with plasma, three liters of physiological saline were used to wash out residual plasma at the same flow rate. The washing was followed by elution of absorbed anti-pig antibodies with 200 ml of 3M NaSCN, pH 7.4. Eluted antibodies in NaSCN were immediately dialyzed against 10 volumes of phosphate-buffered saline, pH 7.4, and concentrated with Amicon's centriprep concentrators (Amicon, Beverly, Mass.) until a concentration of 10 mg protein per ml was reached. This procedure was carried out with six different pig hearts and six different pig kidneys perfused with AB plasma from six different human donors. Yorkshire and Poland China pigs were used as donors of perfused organs.

All anti-pig antibody preparations were then pooled into one common pool for immunization of mice. Human plasma from several individuals and multiple pig organs were used in order to generate a comprehensive pool of human anti-pig antibodies with a wide range of specificities and affinities toward pig antigens. The broad spectrum of human anti-pig antibodies used for immunization of mice was expected to elicit a more extensive anti-idiotypic response, which was a prerequisite for creation of a library of anti-idiotypic antibodies.

(b) Immunization of Mice

Isolated human anti-pig immunoglobulins were used for immunization of young female Balb/c mice. Immunization was carried out by injection of 50 μg of human immunoglobulins, without any adjuvant, biweekly over a period of six months. The injections were administered subcutaneously into the back of the mice, as well as intraperitoneally, alternating the injection site every two weeks. The prolonged immunization schedule was designed to elicit the optimal anti-idiotypic response. Immunization without adjuvant was expected to elicit mouse antibodies capable of recognizing intact conformations of epitopes confined within binding sites of human anti-pig antibodies.

(c) Monitoring of Anti-idiotypic Activity in Mouse Sera

In order to determine the optimal time for fusion and production of hybridomas, mouse sera were analyzed for anti-idiotypic activity every four weeks from the day of first injection. One hundred microliter blood samples were drawn from the tail vein of each mouse. After centrifugation, dilutions of serum were used in competitive enzyme-linked immunoassays (ELISA).

Competitive Enzyme-linked Immunoassay (ELISA)

Cell culture 96-well Costar plates (Cambridge, Mass.) were seeded with pig kidney cells (PK-15) and incubated until the cells were confluent. The plates were then fixed with 1% paraformaldehyde and blocked with 2% milk blocking solution (Kirkegaard and Perry Labs, Gaithesburg, Md.). Mixtures of the human AB serum and immunized mouse sera were prepared which contained increasing quantities of mouse serum and constant concentration of human serum. Each of the prepared mixtures was pipetted in triplicate into the plates with pig cells. After an overnight incubation at 4° C., the plates were washed and a solution of peroxidase-coupled antibody to human immunoglobulins was added. This was followed by a 3 hour incubation at 4° C., washing, and incubation with peroxidase substrate (ABTS, Kirkegaard and Perry Labs) for 30 minutes at room temperature. The optical density of the developed color was measured at 605 nm using a microELISA reader (MR 580, Dyatech, Torrance, Calif.). Anti-idiotypic antibodies in the mouse sera inhibited the binding of human anti-pig antibodies to the pig cells attached on the plate, and the color was diminished proportionally to the concentration of anti-idiotypic antibodies.

(d) Production of Hybridomas

Out of ten mice immunized with human anti-pig (HAP) antibodies, two (HAP4 and HAP5) developed anti-idiotypic titers of 1:8000 and 1:16000, respectively. Both animals were sacrificed and splenectomized. Spleen cells were separately fused with X-63 mouse myeloma cells (commercially available from the American Type Culture Collection., Rockville, Md.) using the well-known polyethylene glycol (PEG) method, and then seeded into 48-well plates containing mouse peritoneal macrophages as a feeder layer. Cells from each fusion (i.e., HAP4 and HAP5) were seeded into 5 plates. One day afterwards fused cells were subjected to selection by hypoxanthine-aminopterin-thymidine (HAT) (Sigma St. Louis, Mo.) -containing RPMI medium supplemented with 10% fetal bovine serum (FBS) (Gibco, Grand Island, N.J.). Fusion plates were maintained in HAT-containing medium for 2 weeks, with regular refeeding every three days. After two weeks the now macroscopically visible hybridomas were weaned from HAT and fed with hypoxanthine-thymidine-containing medium for two days, followed by RPMI with 10% FBS.

Example 2: Screening of Hybridoma Supernates for Anti-idiotypic Antibodies

Each of the above-described fusions (HAP4 and HAP5) resulted in 240 viable hybridomas, giving a total of 480. The great majority of these hybridomas (86%) produced mouse immunoglobulins, as determined by Boehringer's mouse immunoglobulin detection kit (Boehringer, Mannheim, Germany).

To further characterize positive hybridomas, 96 randomly selected supernates from HAP5 fusion were tested in the following manner against human anti-gal IgG, as well as against total human IgG. The human anti-gal IgG was isolated using immunoaffinity chromatography of human AB serum over an immobilized α-gal (1→3) β-gal column (Chembiomed, Edmonton, Alberta, Canada). The immunoglobulins retained by the column were shown to be of an IgG class. These purified anti-gal antibodies were also capable of killing 95% of cultured pig cells in vitro. Human IgG (Cappel, Durham, N.C.) was used as total IgG. Separate ELISA plates were coated with these two human immunoglobulin preparations and blocked. Hybridoma supernates were incubated with coated plates at 4° C. overnight. Each supernate was incubated in duplicate with each human immunoglobulin. After washing off unbound supernate components, the plates were incubated for three hours at room temperature with goat-anti-mouse antibodies coupled to peroxidase, and then washed. The peroxidase substrate (ABTS, Kirkegaard and Perry Labs, Gaithesburg, Md.) was added, and the color determined by a microELISA reader (MR 580 Dynatech, Torrance, Calif.). All wells with optical density three times higher than the background were considered positive. The readings on anti-gal IgG and total IgG were compared, and the supernates were categorized into three groups. The supernates that reacted significantly higher (at least 2×) with anti-gal IgG than with total IgG were considered potentially anti-idiotypic and specific for anti-gal anti-pig antibodies. The supernates that reacted equally well with anti-gal and total human IgG were considered to be specific for immunoglobulin non-idiotypic domains common to all human IgG molecules, and therefore excluded from further analyses. The supernates that showed no reaction with anti-gal IgG and high reactivity with total human IgG were considered potentially anti-idiotypic and specific for non-anti-gal idiotypes.

The screening described above was also carried out with baboon anti-gal IgG and baboon total IgG. The baboon anti-gal IgG was isolated from baboon's AB serum using the above-described immunoaffinity chromatography procedure. The total baboon IgG was isolated from AB serum using the well-known ammonium sulfate precipitation method. These screening procedures were designed to identify hybridomas producing anti-idiotypic antibodies cross-reactive with human and baboon anti-pig antibodies.

The results of screening tests with both human and baboon immunoglobulins showed that 35 out of 96 randomly selected supernates reacted significantly more strongly with human anti-gal IgG, whereas 5 reacted more strongly with total human IgG. The rest of the supernates reacted equally well with both types of immunoglobulins. Four of the anti-gal specific supernates reacted with both human and baboon anti-gal IgG.

These results are in agreement with published data demonstrating that anti-gal antibodies constitute a significant proportion of human anti-pig antibodies. They also suggest the existence of non anti-gal antibodies. They indicate possible cross-reactivity of mouse monoclonal anti-idiotypic antibodies with human and baboon anti-pig antibodies as well.

The 35 hybridomas with specificity for anti-gal antibodies were cloned using 96-well cell culture plates and the limiting dilution procedure well-known to those skilled in the art. A total of 442 clones were generated, 234 of which produced mouse immunoglobulins, and 205 of which were negative. Out of 234 positive clones, 96 reacted more strongly with anti-gal IgG. These clones were characterized in terms of immunoglobulin classes: 29 belonged to IgG, and 67 were IgM. Twelve clones from each immunoglobulin class were tested for their ability to inhibit the binding of human anti-pig antibodies to cultured pig cells in the above-described competitive ELISA. Four of the IgG clones, and five of the IgM clones significantly inhibited binding of human anti-pig antibodies to pig cells.

Example 3: Screening of Monoclonal Anti-idiotypic Antibodies for Neutralization of Hyperacute Rejection (a) In Vitro Killing of Pig Cells by Human and Baboon Serum An assay was carried out on cultured pig cells in order to quantitatively determine the cytotoxic activity of human and baboon sera. Pig kidney cells (PK-15, ATCC, Rockville Pike, Md.) or pig aortic endothelial cells (AG 08472, N.I.A. Aging Cell Culture Repository, Camden, N.J.) were used interchangeably, since both types of cells possess identical cell surface antigens (Koren, E., et al., *Transplant Proc.*, 24(2):598–601, 1992).

The cells ($20 \times 10^4$/ml) were seeded in two-chamber LabTek™ cell culture slides (Nunc, Naperville, Ill.), and grown in DMEM supplemented with 10% FBS (Gibco). After 48 hours of growth, cells were usually semiconfluent, fully differentiated, and well attached to the glass surface of the culture slide. Cells were then gently washed 3× with warm (37° C.) Hank's balanced salt solution (HBSS, Gibco).

De-complemented serum (heat inactivated for 30 minutes at 56° C.) was added (0.5 ml per chamber) to the cells and incubated for 30 minutes at 37° C. The serum was then discarded, the cells were washed with HBSS 2×, and fresh rabbit complement (Pel Freeze Brown Deer, Wis.) diluted in HBSS (1:10) was added. After an additional incubation (30 minutes, 37° C.), the cells were washed again with HBSS 1× and stained with the Live/Dead viability/cytotoxicity kit (Molecular Probes, Eugene, Oreg.) for 30 minutes at 25° C. in the dark. This was followed by washing and drying of slides, then microscopic analysis under an epifluorescent microscope. (Nikon Optiphot, Nikon, Garden City, N.J.).

Staining with the Live/Dead kit allows for clear distinction between live cells, which showed cytoplasmic green fluorescence, and dead cells, which showed dark cytoplasm and red fluorescent nuclei. A total of 400 to 500 cells were counted in each chamber and the results were expressed in terms of the percentage of dead cells. Human and baboon sera with rabbit complement added usually killed 90–95% cells. Heat-inactivated sera without complement added killed only 5–10% cells, whereas rabbit complement alone killed 4–8% cells.

(b) Pre-incubation of Human and Baboon Sera with Anti-idiotypic Monoclonal Antibodies Inhibits the Cytotoxic Activity Against Pig Cells in Vitro Nine of the clones described in Example 2 significantly inhibited binding of human anti-pig antibodies to pig cells. Six of these nine clones were grown in T-75 flasks in order to produce larger quantities (100 ml) of supernates. These clones included three IgG producers (HAP-5eB$_8$D$_3$, HAP-5eB$_3$B$_1$ and HAP-5dC$_4$) and three IgM producers (HAP-5dE$_2$A$_2$, HAP-5dE$_2$C$_3$, HAP-5eF$_1$D$_3$). HAP-5dC$_4$ is one of the antibodies that binds to both human and baboon anti-gal antibodies.

Each of the supernates was concentrated using Amicon's concentrators (Amicon, Beverly, Mass.) to a volume of 5 ml. Each of the concentrated supernates was mixed with sera both separately and in various combinations, and incubated at 37° C. for one hour. The mixtures were then added to pig cells, and the above-described cytotoxicity assay was carried out. Various quantities of each supernate (25, 50, 100 and 250 µl) were also analyzed in order to determine if the protective activity was dependent on the concentration of anti-idiotypic antibodies. The results demonstrated that all six monoclonal anti-idiotypic antibodies protected pig cells to some degree. As used herein, the phrase "protected pig cells" means the monoclonal anti-idiotypic antibodies reduced the cytotoxicity of the human or baboon sera in the above-described cytotoxicity assay. HAP-5dE$_2$A$_2$ and HAP-5eF$_1$D$_6$ protected 60 and 65% of pig cells, respectively, at their highest concentrations. HAP-5dE$_2$C$_3$ showed 50% protection, and HAP-5eB$_8$D$_3$ showed 35% protection. The remaining clones, HAP-5eB$_1$B$_1$ and HAP-5dF$_4$, each protected 30% of pig cells at their highest concentrations. HAP-5dC$_4$ protected pig cells from cytotoxic activity of both human and baboon sera. In each case, the two highest quantities of supernates added (i.e., 100 µl and 250 µl) had the same protective effects, indicating the complete saturation of corresponding anti-pig antibodies. Interestingly, various combinations of supernates provided higher levels of protection. HAP-5dE$_2$A$_2$ combined with HAP-5dE$_2$C$_3$ and HAP-5eB$_8$D$_3$ protected 80% of the pig cells. However, none of the combinations could completely protect the cells.

These results suggest that the selected monoclonal antibodies recognize various subsets of anti-gal anti-pig antibodies since all of them were originally shown to bind anti-gal antibodies.

These results also indicate that a comprehensive library of monoclonal anti-idiotypic antibodies is necessary to completely protect pig cells. Since the six selected antibodies described herein represent only a fraction of the overall number of available hybridomas, it is expected that such a comprehensive library can be created upon the completion of screening.

Example 4: Immobilization of Anti-idiotypic Monoclonal Antibodies and Isolation of Human Anti-pig Antibody Subsets HAP-5dE$_2$A$_2$, HAP-5dE$_2$C$_3$ and HAP-5eB$_8$D$_3$ clones were injected into pristane-primed Balb-c mice in order to produce antibodies in ascites, a procedure well known to those skilled in the art. Ten milliliters of ascites from each clone were used to purify each set of antibodies and to couple them to the Affi-Gel™ 10 (BioRad, Richmond, Calif.) according to the manufacturer's instructions. Briefly, Affi-Gel™ couples IgG molecules via primary amino groups on the antibody molecules to an agarose support. Each antibody solution (3 ml 0.1M MOPS, pH 7.5, containing 40 mg protein) was combined with 2 ml of Affi-Gel™ gel. The gel slurry was mixed at 4° C. for 2 hours, and then stripped with 7M urea containing 1M NaCl to remove the uncoupled protein. Three 15 ml immunoaffinity columns were prepared and used to isolate corresponding anti-pig antibodies from 2 ml of human AB serum. In each case, the human anti-pig antibodies were eluted from the columns with 3M NaSCN and concentrated to the original 2 ml volume of serum. These antibodies were then used in the cytotoxicity assays separately, and in combinations. The human antibody eluted from the HAP-5dE$_2$A$_2$ column killed 53% of the pig cells, while those eluted from the HAP-5dE$_2$C$_3$ and HAP-5eB$_8$D$_3$ columns killed 46 and 42%, respectively. All three human antibodies, used in combination, killed 85% of the cells. These results demonstrate the feasibility of isolation and removal of various subsets of anti-pig antibodies.

Example 5: Production of Human Recombinant Antibodies

The Recombinant Phage Antibody System (RPAS) designed for mouse recombinant antibodies is available in kit form from Pharmacia-LKB Biotechnology. This methodology was developed by Cambridge Antibody Technology (CAT, Cambridge, UK) for both mouse and human recombinant antibodies. Although the following example does not describe recombinant anti-idiotypic antibodies, it does demonstrate the ability of one of ordinary skill in the art to produce human recombinant antibodies using the present disclosure in combination with CAT's methodology.

This experiment was designed to generate human recombinant antibodies against 60 KD Ro antigen, and to examine the binding of these antibodies to the Ro sequence. Peripheral blood B lymphocytes were isolated from an anti-Ro positive patient, and mRNA was extracted from these cells. The isolated mRNA was used to make cDNA by reverse transcription using heavy chain and light chain specific primers. The polymerase chain reaction (PCR) was used to amplify the IgG heavy (VH) and light chain (VL) variable genes using family-based primers. Genes encoding for single-chain Fv fragments (ScFv) were assembled by randomly combining the VH and VL products through a linker sequence using PCR. A library including a total of $10^6$ gene combinations was then cloned into fd phage and displayed on the phage surface. Anti-Ro positive phage were enriched by four consecutive rounds of growth and panning in tubes coated with human 60 KD Ro antigen. Twenty-six clones with variable binding reactivity to the Ro antigen were identified using ELISA with Ro-coated plates. Ten of these recombinant ScFv antibodies were also tested against two other autoantigens, nRNP and Sm autoantigens, as well as bovine serum albumin, and none was found to bind to these antigens. Furthermore, the binding of these recombinant ScFv to the Ro antigen immobilized on ELISA plate was inhibited by the Ro antigen added to ScFv in a fluid phase. These data will be published by Huang, S. C., Koren, E., and Harley, J. B., in a paper entitled, "Human Recombinant Monoclonal Antibodies to 60 kD Ro. Autoantigen," at the American College of Rheumatology, 57th Annual Scientific Meeting, San Antonio, Nov. 7–11, 1993.

Modifications and variations of the present method of using anti-idiotypic monoclonal antibodies to inhibit rejection of transplanted animal tissues will be obvious to those skilled in the art from the foregoing detailed description of the invention. Such modifications and variations are intended to come within the scope of the appended claims.

We claim:

1. A composition for inhibiting the rejection of tissues from a donor animal of one species transplanted to a recipient animal of another species comprising anti-idiotypic antibodies, or antigen binding fragments thereof, specifically immunoreactive with the anti-donor animal antibodies which cause complement mediated cytolysis of cells from the donor animal of the recipient animal, in a pharmaceutically acceptable carrier.

2. The composition of claim 1, wherein the recipient animal is a human.

3. The composition of claim 1, wherein the donor animal is a pig.

4. The composition of claim 1, wherein the antigen binding fragments are selected from the group consisting of $Fab_1$, $Fab_2$, and single-chain variable fragments.

5. The composition of claim 1 wherein the anti-idiotypic antibodies, or antigen binding fragments thereof, are humanized or of human origin and bind to anti-animal antibodies.

6. The composition of claim 5 wherein the human anti-idiotypic antibodies are produced from human B cells.

7. The composition of claim 5 wherein the anti-idiotypic antibodies are produced by humanization of anti-idiotypic antibodies derived from a first animal species which are immunoreactive with human antibodies immunoreactive with epitopes present in a second non-human donor animal species.

8. The composition of claim 5 wherein the anti-idiotypic antibodies bind to human anti-gal antibodies.

9. The composition of claim 5 wherein the anti-idiotypic antibodies are bound to an immobilized substrate.

10. The composition of claim 9 wherein the immobilized substrate is part of an extracorporeal device.

11. The composition of claim 9 wherein the substrate is a chromatographic material.

12. The composition of claim 5 wherein the antibodies further comprise a detectable label.

13. The composition of claim 7 wherein the first animal species is a mouse.

14. The composition of claim 7 wherein the second animal species is a pig.

* * * * *

UNITED STATES PATENT AND TRADEMARK OFFICE
CERTIFICATE OF CORRECTION

PATENT NO. : 5,728,812
DATED : March 17, 1998
INVENTOR(S) : Eugen Koren and David K.C. Cooper It is certified that error appears in the above-indentified patent and that said Letters Patent is hereby corrected as shown below:

On the title page:

item [73] Assignees, after "Oklahoma Medical Research Foundation", please delete "Baptist Medical Center of Oklahoma, Inc." and insert --Integris Baptist Medical Center, Inc.-- in place thereof.

Signed and Sealed this

Tenth Day of August, 1999

Attest:

Q. TODD DICKINSON

Attesting Officer

Acting Commissioner of Patents and Trademarks